(12) United States Patent
Bernstein et al.

(10) Patent No.: US 8,900,643 B2
(45) Date of Patent: Dec. 2, 2014

(54) METHOD OF TREATMENT USING A THERAPEUTIC AGENT FOR INTRANASAL ADMINISTRATION

(71) Applicants: Jonathan Bernstein, Cincinnati, OH (US); Wayne Jeffrey Perry, Schenectady, NY (US)

(72) Inventors: Jonathan Bernstein, Cincinnati, OH (US); Wayne Jeffrey Perry, Schenectady, NY (US)

(73) Assignee: Hi-Tech Pharmacal Co., Inc., Amityville, NY (US)

( * ) Notice: Subject to any disclaimer, the term of this patent is extended or adjusted under 35 U.S.C. 154(b) by 0 days.

(21) Appl. No.: 14/082,890

(22) Filed: Nov. 18, 2013

(65) Prior Publication Data

US 2014/0147531 A1 May 29, 2014

Related U.S. Application Data

(63) Continuation of application No. 13/234,862, filed on Sep. 16, 2011, now abandoned, and a continuation-in-part of application No. 12/849,088, filed on Aug. 3, 2010, now abandoned, which is a continuation of application No. 11/731,657, filed on Mar. 30, 2007, now abandoned.

(60) Provisional application No. 61/405,390, filed on Oct. 21, 2010.

(51) Int. Cl.
| | | |
|---|---|---|
| *A01N 65/00* | (2009.01) | |
| *A61K 9/08* | (2006.01) | |
| *A61K 36/81* | (2006.01) | |
| *A61K 9/00* | (2006.01) | |

(52) U.S. Cl.
CPC . *A61K 36/81* (2013.01); *A61K 9/08* (2013.01); *A61K 9/0043* (2013.01)
USPC ........................................................ 424/725

(58) Field of Classification Search
None
See application file for complete search history.

(56) References Cited

U.S. PATENT DOCUMENTS

2004/0161435 A1  8/2004  Gupta

OTHER PUBLICATIONS

Civil Action No. CV 12-2429 (ADS) Answer and Cross-Claims of Dynova Laboratories, Inc. filed Jul. 17, 2012.
Civil Action No. 12-cv-2897 (ADS) Answer and Cross-Claims of Dynova Laboratories, Inc. and Sicap Industries, LLC filed Jul. 17, 2012.
Civil Action No. CV 12-2897 (ADS-AKT) Answer and Cross-Claims filed Jul. 17, 2012.
Case 2:12-cv-02897-ADS-AKT Document 1 Class Action Complaint filed Jun. 8, 2012.
Case 1:12-cv-02429-BMC Document 1 Class Action Complaint filed May 6, 2012.
Civil Action No. 12-CV-2429 (ADS) (AKT) Consolidated Class Action Complaint filed Jan. 9, 2013.
Dynova Labs Supporting Clinical Study Abstracts.
Civil Action No. CV 12-2429 (ADS-AKT) Amended Answer and Cross-Claims filed Jul. 17, 2012.
Amended Answer with Cross-Claims; Civ. Action No. CV-12-2429 filed Jun. 28, 2012.
Amended Answer with Cross-Claims; Civ. Action No. CV-12-2897 filed Dec. 4, 2012.
Dynovalabs "Supporting Clinical Study Abstracts" Retrieved Jan. 24, 2012.
Zhang Fanying, et al. "Clinical study of capsaicin in the treatment of allergic rhinitis" J. Clin. Otorhinolaryngol (China), Nov. 1999, vol. 13, No. 11.
Par Stjarne, et al. "Capsaicin Desensitization of the Nasal Mucosa Reduces Symptoms upon Allergen Challenge in Patients with Allergic Rhinitis" Acta Otolaryngol (Stockh) 1998; 118: p. 235-239.
Cheng J, et al. "Capsaicin for allergic rhinitis in adults (Review)" The Cochrane Collaboration, published in The Cochrane Library 2006, Issue 2.
J. B. Van Rijswijk , et al. "Intranasal capsaicin reduces nasal hyperreactivity in idiopathic rhinitis: a double-blind randomized application regimen study" European Journal of Allergy and Clinical Immunology, vol. 58, No. 8, Aug. 2003.
G. Wolf, et al. "Treatment of Non-Specific Hyper-reflectory Rhinopathy(Vasomotoric Rhinitis) with Capsaicin" Laryngo-Rhino-Otol. 74, (1995), p. 289-293.
Zhang Ruxin, et al. "Clinical Observation and Therapeutic Mechanism of Blocking Agent of Substance P Nerves in the Treatment of Perennial Allergic Rhinitis" Chinese Journal of Otorhinolaryngology, vol. 30, No. 3, Jun. 10. 1995.
Russell A. Settipane, MD, et al. Update on nonallergic rhinitis. Annals of Allergy, Asthma, & Immunology, May 2001; 86:494-507; quiz-8.
Dana V. Wallace, et al. The diagnosis and management of rhinitis: an updated practice parameter. J Allergy Clin Immunol Aug. 2008; 122:S1-84.
Jonathan A. Bernstein. Characteristics of Non-Allergic Vasomotor Rhintiis. World Allergy Journal, Jun. 2009; 2:102-5.
Michael A. Kaliner. Classification of Nonallergic Rhinitis Syndromes With a Focus on Vasomotor Rhinitis, Proposed to be known henceforth as Nonallergic Rhinopathy. World Allergy Journal Jun. 2009, 2:98-101.
Russell A. Settipane, MD. Demographics and epidemiology of allergic and nonallergic rhinitis. Allergy and Asthma Proc Jul.-Aug. 2001; vol. 22, No. 4:185-9.
Dominique Brandt, MA et al. Questionnaire evaluation and risk factor identification for nonallergic vasomotor rhinitis. Annals of Allergy, Asthma, & Immunology, Apr. 2006; 96:526-32.
R. Garay. Mechanisms of vasomotor rhinitis. Allergy 2004; 59 Suppl 76:4-9; discussion-10.
James N. Baraniuk, MD. Sensory, parasympathetic, and sympathetic neural influences in the nasal mucosa. J Allergy Clin Immunol Dec. 1992; vol. 90, No. 6, Part 2:1045-50.

(Continued)

*Primary Examiner* — Michael Meller

(57) ABSTRACT

The present invention provides a composition suitable for intranasal administration comprising capsaicin, dihydrocapsaicin, and nordihydrocapsaicin in the form of capsicum used as a therapeutic agent.

3 Claims, 4 Drawing Sheets

(56) References Cited

OTHER PUBLICATIONS

A.S. Jones. Autonomic reflexes and non-allergc rhinitis. Allergy 1997; 52(suppl. 36):14-19.

Nobuhiko Seki, et al. Expression and localization of TRPV1 in human nasal mucosa. Rhinology 2006; 44:128-34.

Charles H. Banov, MD, et al. Efficacy of azelastine nasal spray in the treatment of vasomotor (perennial nonallergic) rhinitis. Annals of Allergy, Asthma, & Immunology Jan. 2001; vol. 86:28-35.

J.W. Georgitis, et al. Ipratropium bromide nasal spray in nonallergic rhinitis: efficacy, nasal cytological response and patient evaluation on quality of life. Clinical and Experimental Allergy 1994; vol. 24:1049-55.

Phillip L. Lieberman, et al. Azelastine nasal spray: a review of pharmacology and clinical efficacy in allergic and nonallergic rhinitis. Allergy and Asthma Proc. Mar.-Apr. 2003; vol. 24, No. 2:95-105.

G.K. Scadding, et al. A placebo-controlled study of fluticasone propionate aqueous nasal spray and beclomethasone dipropionate in perennial rhinitis: efficacy in allergic and non-allergic perennial rhinitis. Clinical and Experimental Allergy 1995;vol. 25:737-43.

C. Ciprandi. Treatment of nonallergic perennial rhinitis. Allergy 2004: 59 (Suppl 76);16-23; discussion-3.

H.M. Blom, et al. Intranasal capsaicin is efficacious in non-allergic, non-infectious perennial rhinitis. A placebo-controlled study. Clinical and Experimental Allergy 1997: vol. 27:796-801.

H.M. Blom, et al. The long-term effects of capsaicin aqueous spray on the nasal mucosa. Clinical and Experimental Allergy 1998; vol. 28:1351-8.

J.S. Lacroix, et al. Improvement of symptoms of non-allergic chronic rhinitis by local treatment with capsaicin. Clinical and Experimental Allergy 1991; vol. 21:595-600.

A.M. Sanico, et al. Comparison of nasal mucosal responsiveness to neuronal stimulation in non-allergic and allergic rhinitis: effects of capsaicin nasal challenge. Clinical and Experimental Allergy 1998; 28:92-100.

J.B. Van Rijswijk, et al. Intranasal capsaicin reduces nasal hyper-reactivity in idiopathic rhinitis: a double-blind randomized application regimen study. Allergy 2003; 58:754-61.

METHOD OF TREATMENT USING A THERAPEUTIC AGENT FOR INTRANASAL ADMINISTRATION

CROSS REFERENCE TO RELATED APPLICATIONS

This application claims priority to U.S. patent application Ser. No. 13/234,862, filed Sep. 16, 2011, which is and which is hereby incorporated by reference in its entirety for all purposes. U.S. Patent Application No. 61/405,390, filed Oct. 21, 2010, and is a continuation-in-part of U.S. patent application Ser. No. 12/849,088, filed Aug. 3, 2010, which is a continuation of U.S. patent application Ser. No. 11/731,657, filed Mar. 30, 2007, now abandoned, all of which are herein incorporated by reference in their entirety for all purposes. This application is also related to U.S. patent application Ser. No. 11/731,656, filed Mar. 30, 2007, now abandoned, which is herein incorporated by reference in its entirety for all purposes.

FIELD OF THE INVENTION

The present invention relates to a method of treatment using a therapeutic agent capable of intranasal administration comprising capsicum and/or capsaicinoids as the therapeutic agent.

BACKGROUND OF THE INVENTION

Non-allergic rhinitis ("NAR") affects millions of Americans, but the mechanism(s) remains unknown. Transient receptor potential vanilloid-1 ("TRPV1") may be involved, as single dose studies of intranasal capsaicin, a TRPV1 agonist, have demonstrated reduced nasal congestion in rhinitis subjects.

Chronic rhinitis is defined as persistent inflammation of the mucosal membranes lining the nasal cavity, characterized by symptoms of nasal congestion, rhinorrhea, sneezing and itching with or without post-nasal drainage. (Settipane R A, Lieberman P. Update on nonallergic rhinitis. Ann Allergy Asthma Immunol 2001; 86:494-507; quiz −8. Wallace D V, Dykewicz M S, Bernstein D I, Blessing-Moore J, Cox L, Khan D A, et al. The diagnosis and management of rhinitis: an updated practice parameter. J Allergy Clin Immunol 2008; 122:S1-84.) A diagnosis requires the exclusion of structural abnormalities and underlying medical conditions that can manifest with rhinitis symptoms. (Settipane R A, Lieberman P. Update on nonallergic rhinitis. Ann Allergy Asthma Immunol 2001; 86:494-507; quiz −8. Wallace D V, Dykewicz M S, Bernstein D I, Blessing-Moore J, Cox L, Khan D A, et al. The diagnosis and management of rhinitis: an updated practice parameter. J Allergy Clin Immunol 2008; 122:S1-84.) Broadly defined, rhinitis can be divided into inflammatory and non-inflammatory rhinitis. (Wallace D V, Dykewicz M S, Bernstein D I, Blessing-Moore J, Cox L, Khan D A, et al. The diagnosis and management of rhinitis: an updated practice parameter. J Allergy Clin Immunol 2008; 122:S1-84. Bernstein J A. Characteristics of Non-Allergic Rhintiis. World Allergy Journal 2009; 2:102-5.)

Inflammatory rhinitis includes seasonal or perennial allergic rhinitis, entopic rhinitis and non-allergic rhinitis eosinophilic syndrome ("NARES") whereas non-inflammatory rhinitis includes vasomotor rhinitis ("VMR"), commonly referred to as idiopathic rhinitis, and other non-allergic rhinitis conditions such as rhinitis medicamentosa, gustatory rhinitis and hormonally-induced rhinitis. (Bernstein J A. Characteristics of Non-Allergic Rhintiis. World Allergy Journal 2009; 2:102-5. Kaliner M. Classification of Nonallergic Rhinitis Syndromes With a Focus on Vasomotor Rhinitis, Proposed to be known henceforth as Nonallergic Rhinopathy. World Allergy Journal 2009; 2:98-101.) Since patients with allergic rhinitis often exhibit significant symptoms in response to irritant triggers, clinicians have postulated that allergic and non-allergic rhinitis components often co-exist and have therefore referred to this condition as "mixed rhinitis" ("MR"). (Bernstein J A, Rezvani, M. Mixed Rhinitis: A New Subclass of Chronic Rhinitis. In: Kaliner M, ed. Current Review of Rhinitis, 2nd ed 2006; Philadelphia, Pa.:69-78.) Cross-sectional questionnaire survey studies have estimated that up to 75% of chronic rhinitis patients have either non-allergic or mixed rhinitis. (Settipane R A. Demographics and epidemiology of allergic and nonallergic rhinitis. Allergy Asthma Proc 2001; 22:185-9.)

Currently non-allergic rhinitis ("NAR") conditions are diagnoses by exclusion, as the mechanism(s) of this disorder is unknown and therefore, there are no specific biomarkers or tests that establish a definitive diagnosis. (Bernstein J A. Characteristics of Non-Allergic Rhintiis. World Allergy Journal 2009; 2:102-5. Kaliner M. Classification of Nonallergic Rhinitis Syndromes With a Focus on Vasomotor Rhinitis, Proposed to be known henceforth as Nonallergic Rhinopathy. World Allergy Journal 2009; 2:98-101. Brandt D, Bernstein J A. Questionnaire evaluation and risk factor identification for nonallergic vasomotor rhinitis. Ann Allergy Asthma Immunol 2006; 96:526-32. Garay R. Mechanisms of vasomotor rhinitis. Allergy 2004; 59 Suppl 76:4-9; discussion −10.) The most popular mechanism postulated for non-allergic rhinitis has been an autonomic imbalance between the sympathetic and parasympathetic nervous system resulting in parasympathetic hyperactivity leading to nasal congestion and drainage. (Baraniuk J N. Sensory, parasympathetic, and sympathetic neural influences in the nasal mucosa. J Allergy Clin Immunol 1992; 90:1045-50. Jones A S. Autonomic reflexes and non-allergic rhinitis. Allergy 1997; 52:14-9.) Recently, transient receptor protein ("TRP") ion channel activation leading to trigeminal nerve depolarization has been postulated to play an important role in NAR, as these ubiquitous receptors can be activated by different temperatures, chemicals, osmolality and other physical stimuli that are well recognized triggers of symptoms in NAR patients. (Bernstein J A. Characteristics of Non-Allergic Rhintiis. World Allergy Journal 2009; 2:102-5. Brandt D, Bernstein J A. Questionnaire evaluation and risk factor identification for nonallergic vasomotor rhinitis. Ann Allergy Asthma Immunol 2006; 96:526-32. Seki N, Shirasaki H, Kikuchi M, Sakamoto T, Watanabe N, Himi T. Expression and localization of TRPV1 in human nasal mucosa. Rhinology 2006; 44:128-34.)

Because mechanisms of NAR are poorly elucidated, there are still only a few medications approved for the treatment of this condition. Although clinical studies have found that the intranasal antihistamines, azelastine and olopatidine, intranasal ipratropium bromide and intranasal corticosteroids are relatively effective in relieving symptoms related to NAR, it is unclear how they are mechanistically exerting their effect. (Banov C H, Lieberman P. Efficacy of azelastine nasal spray in the treatment of vasomotor (perennial nonallergic) rhinitis. Ann Allergy Asthma Immunol 2001; 86:28-35. Georgitis J W, Banov C, Boggs P B, Dockhorn R, Grossman J, Tinkelman D, et al. Ipratropium bromide nasal spray in non-allergic rhinitis: efficacy, nasal cytological response and patient evaluation on quality of life. Clin Exp Allergy 1994; 24:1049-55. Lieberman P L, Settipane R A. Azelastine nasal spray: a review of pharmacology and clinical efficacy in allergic and nonallergic rhinitis. Allergy Asthma Proc 2003; 24:95-105. Scadding G K, Lund V J, Jacques L A, Richards D H. A placebo-controlled study of fluticasone propionate aqueous nasal spray and beclomethasone dipropionate in perennial rhinitis: efficacy in allergic and non-allergic perennial rhinitis. Clin Exp Allergy 1995; 25:737-43. Ciprandi G. Treatment of nonallergic perennial rhinitis. Allergy 2004; 59 Suppl 76:16-22; discussion −3.)

Capsaicin is a pungent substance found in *capsicum* spp. (red pepper) that is known to ablate sensory nerve fibers in NAR patients leading investigators to postulate a role for afferent C-fibers in NAR. (Blom H M, Van Rijswijk J B, Garrelds I M, Mulder P G, Timmermans T, Gerth van Wijk R. Intranasal capsaicin is efficacious in non-allergic, non-infectious perennial rhinitis. A placebo-controlled study. Clin Exp Allergy 1997; 27:796-801.) This observation was supported by early placebo controlled studies that treated NAR patients with topical capsaicin and found significant improvement in symptom scores compared to placebo without changes in levels of mast cell mediators (i.e., leukotrienes, prostaglandin (PGD2) or tryptase) indicating that the effect of this medication was not due to reduction in mast-cell mediated inflammation. (Blom H M, Van Rijswijk J B, Garrelds I M, Mulder P G, Timmermans T, Gerth van Wijk R. Intranasal capsaicin is efficacious in non-allergic, non-infectious perennial rhinitis. A placebo-controlled study. Clin Exp Allergy 1997; 27:796-801. Blom H M, Severijnen L A, Van Rijswijk J B, Mulder P G, Van Wijk R G, Fokkens W J. The long-term effects of capsaicin aqueous spray on the nasal mucosa. Clin Exp Allergy 1998; 28:1351-8.)

Subsequently, it was discovered that capsaicin exerted its activity through activation of the TRP vanilloid-1 ("TRPV1") ion channel which leads to desensitization of nasal sensory neural fibers and reduction in nasal hyperresponsiveness. (Seki N, Shirasaki H, Kikuchi M, Sakamoto T, Watanabe N, Himi T. Expression and localization of TRPV1 in human nasal mucosa. Rhinology 2006; 44:128-34.) Single intermittent short term dosing studies with intranasal capsaicin in AR and NAR have confirmed that intranasal capsaicin is effective at reducing nasal congestion and discharge. (Blom H M, Van Rijswijk J B, Garrelds I M, Mulder P G, Timmermans T, Gerth van Wijk R. Intranasal capsaicin is efficacious in non-allergic, non-infectious perennial rhinitis. A placebo-controlled study. Clin Exp Allergy 1997; 27:796-801. Blom H M, Severijnen L A, Van Rijswijk J B, Mulder P G, Van Wijk R G, Fokkens W J. The long-term effects of capsaicin aqueous spray on the nasal mucosa. Clin Exp Allergy 1998; 28:1351-8. Lacroix J S, Buvelot J M, Polla B S, Lundberg J M. Improvement of symptoms of non-allergic chronic rhinitis by local treatment with capsaicin. Clin Exp Allergy 1991; 21:595-600. Sanico A M, Philip G, Proud D, Naclerio R M, Togias A. Comparison of nasal mucosal responsiveness to neuronal stimulation in non-allergic and allergic rhinitis: effects of capsaicin nasal challenge. Clin Exp Allergy 1998; 28:92-100. Van Rijswijk J B, Boeke E L, Keizer J M, Mulder P G, Blom H M, Fokkens W J. Intranasal capsaicin reduces nasal hyperreactivity in idiopathic rhinitis: a double-blind randomized application regimen study. Allergy 2003; 58:754-61.)

However, the concentration of capsaicin used and found effective in these studies, ranging from 30 ppm to 300 ppm, was very irritating and required a physician to co-administer a local anesthetic making it impractical and intolerable for patients to self-administer the composition or use this treatment long term. (Blom H M, Van Rijswijk J B, Garrelds I M, Mulder P G, Timmermans T, Gerth van Wijk R. Intranasal capsaicin is efficacious in non-allergic, non-infectious perennial rhinitis. A placebo-controlled study. Clin Exp Allergy 1997; 27:796-801. Blom H M, Severijnen L A, Van Rijswijk J B, Mulder P G, Van Wijk R G, Fokkens W J. The long-term effects of capsaicin aqueous spray on the nasal mucosa. Clin Exp Allergy 1998; 28:1351-8. Lacroix J S, Buvelot J M, Polla B S, Lundberg J M. Improvement of symptoms of non-allergic chronic rhinitis by local treatment with capsaicin. Clin Exp Allergy 1991; 21:595-600. Van Rijswijk J B, Boeke E L, Keizer J M, Mulder P G, Blom H M, Fokkens W J. Intranasal capsaicin reduces nasal hyperreactivity in idiopathic rhinitis: a double-blind randomized application regimen study. Allergy 2003; 58:754-61.) Applicant is not aware of any prior studies disclosing, teaching or suggesting a composition comprising capsicum/capsaicin present in an effective concentration, that may be self-administered as a mono-therapy by the user. Furthermore, Applicant is not aware of any studies demonstrating clinical efficacy of capsicum/capsaicin at concentrations 10% or less of the dosages used in previous rhinitis clinical trials. What is needed in the industry is a composition comprising capsicum/capsaicin that may be administered intranasally in an effective concentration, allowing the user to self-administer the composition without the need for the user to visit a physician's office for each treatment.

According to an embodiment of the present invention, it has been unexpectedly discovered that certain concentrations of capsicum comprising capsaicinoids, including capsaicin, may be self-administered by the user and provide relief from symptoms. Previously it has not been possible to deliver an effective concentration of capsicum intranasally without causing such discomfort to the user requiring the use of an adjunct to desensitize the nasal membranes in order to administer the capsicum. What is needed in the industry is a composition comprising capsicum/capsaicin that is effective in relieving symptoms, but can be used without causing discomfort to the user or requiring adjunct agents.

Applicant is not aware of any prior studies investigating the immediate or short-term relief of symptoms provided by the intranasal administration of capsicum as disclosed in the present application. In addition, Applicant is not aware of any prior studies disclosing that a low homeopathic dilution of capsicum is clinically effective for the treatment of rhinitis.

What is needed in the industry is a nasally administered composition that provides a rapid onset of relief for rhinitis subjects. What is needed in the industry is an intranasally administered composition having a rapid onset of action and significant reduction of symptoms, that is an attractive mono-therapy or adjunctive therapy for the management of rhinitis symptoms, including, but not limited to, chronic rhinitis symptoms. What is needed in the industry is an intranasally administered composition having a quick onset of action with an average time to first relief in less than thirty minutes, less than five minutes, and even less than one minute.

Currently available over the counter ("OTC") medicated nasal sprays for the relief of rhinitis symptoms necessarily contain labels with a warning indicating that the product should not be used for more than three days. Extended use of these known products leads to the occurrence of rebound congestion and the potential for addiction. These known OTC products are not suitable for use by those with symptoms that last longer than three days, including those suffering chronic conditions, and those suffering from chronic rhinitis symptoms.

What is needed in the industry is an intranasally administered composition that is well-tolerated with prolonged treatment results and with substantially no alteration or impairment in olfaction. What is needed in the industry is an intranasal composition wherein users experience little to no rebound congestion. What is needed in the industry is an intranasal composition wherein use of the composition results in an improvement in olfaction versus placebo after continued use.

What is needed in the industry is an intranasally administered composition wherein during a treatment period is significantly effective at improving nasal congestion, sinus pressure, sinus pain and headache compared to placebo. What is needed in the industry is a nasally administered composition that provides safe, sustained relief over the course of a treatment period. What is needed in the industry is a nasally administered composition that works fast and is safe.

What is needed in the industry is an intranasally administered composition that provides relief from at least one of nasal congestion, sinus pressure and sinus pain with an improved therapeutic response that continues over time with nasal congestion, sinus pressure, sinus pain and headache significantly improved at about 5, 10, 15 and 30 minutes and persists for nasal congestion and sinus pain through the longest time point measured.

SUMMARY OF THE INVENTION

An embodiment of the present invention is a composition comprising an aqueous homeopathic dilution of *capsicum*, wherein the composition is suitable for intranasal administration to a human in need thereof, that provides fast relief, wherein the first relief from at least one rhinitis symptom occurs within about 30 minutes of administration. The homeopathic dilution of capsicum may be at a concentration of about 0.00060% to about 0.010% w/w or containing about 0.1 to about 2.0 ppm total capsaicinoids. The homeopathic dilution of capsicum may be at a concentration of about 0.0020% to about 0.0080% w/w or containing about 0.3 to about 1.5 ppm total capsaicinoids. The homeopathic dilution of capsicum may be at a concentration of about 0.0030% to about 0.0080% w/w or containing about 0.5 to about 1.5 ppm total capsaicinoids. The composition may comprise rosemary extract at a concentration of about 0.02% to about 0.25% w/w, at a concentration of about 0.05% to about 0.10% w/w, or at a concentration of about 0.06% to about 0.07% w/w. The first relief from at least one symptom may occur within about 30 minutes of administration, within about 15 minutes of administration, within about 5 minutes of administration, within about 3 minutes of administration, or within about 1 minute of administration. The rhinitis symptoms relieved may comprise at least one of nasal congestion, sinus pressure, sinus pain, headache, or a combination thereof. The composition may comprise eucalyptol at a concentration of about 0.07% to about 0.15% w/w, vegetable glycerin at a concentration of about 3.5% to about 5.0% w/w, vegetable glycerin at a concentration of about 3.9% to about 4.5% w/w, ascorbic acid at a concentration of about 0.10% to about 0.90% w/w, sea salt at a concentration of about 0.40% to about 1.2% w/w, potassium sorbate at a concentration of about 0.05% to about 0.3%, or a combination thereof. It is surprising and unexpected that a homeopathic dose of capsicum, such as, but not limited to, 5% or less of therapeutic doses known in the art, is still an effective dose. As such, it is surprising and unexpected that a homeopathic dose of capsicum would still provide a significant benefit as shown in an embodiment of the present invention.

An embodiment of the present invention is a composition comprising an aqueous solution of capsicum at a concentration of about 0.00060% to about 0.010% w/w, or containing about 0.1 to about 2.0 ppm total capsaicinoids, including, but not limited to, capsaicin, wherein the composition is suitable for intranasal administration to a human in need thereof, wherein the first relief from at least one rhinitis symptom occurs within about 30 minutes of administration, and wherein the symptoms may comprise at least one of nasal congestion, sinus pressure, sinus pain, headache or a combination thereof. In an embodiment the aqueous solution of capsicum comprises a homeopathic dilution of capsicum. In an embodiment the aqueous solution of capsicum comprises a homeopathic dilution of Capsicum annum. In an embodiment, the aqueous solution of capsicum may be at a concentration of about 0.0020% to about 0.0080% w/w, or containing about 0.3 to about 1.5 ppm total capsaicinoids. In an embodiment the aqueous solution of capsicum may be at a concentration of about 0.0030% to about 0.0080% w/w, or containing about 0.5 to about 1.5 ppm total capsaicinoids.

An embodiment of the present invention is a composition comprising an aqueous solution of capsicum at a concentration of about 0.00060% to about 0.010% w/w, resulting in about 0.1 to about 2.0 ppm total capsaicinoids. An embodiment may also comprise rosemary extract at a concentration of about 0.02% to about 0.25% w/w, or comprise rosemary extract at a concentration of about 0.05% to about 0.10% w/w or about 0.06% to about 0.07% w/w, wherein the composition is suitable for intranasal administration to a human in need thereof, wherein the first relief from at least one rhinitis symptom occurs within about 30 minutes of administration, and wherein the symptoms comprise at least one of nasal congestion, sinus pressure, sinus pain, headache or a combination thereof. In an embodiment the aqueous solution of capsicum may or may not comprise a homeopathic dilution of capsicum. In an embodiment the aqueous solution of capsicum may be at a concentration of about 0.0020% to about 0.0080% w/w, or containing about 0.3 to about 1.5 ppm total capsaicinoids. In an embodiment the aqueous solution of capsicum may be at a concentration of about 0.0030% to about 0.0080% w/w, or containing about 0.5 to about 1.5 ppm total capsaicinoids. It is surprising and unexpected that a homeopathic dose of capsaicin, such as, but not limited to, 5% or less of therapeutic doses known in the art, is still an effective dose. As such, it is surprising and unexpected that a homeopathic dose of capsicum would still provide a significant benefit as shown in an embodiment of the present invention.

A surprising and unexpected result according to an embodiment of the present invention is that the presence of the rosemary extract acts to increase the tolerability of the capsicum in the composition to the user. Applicant is not aware of any disclosure, teaching, or suggestion in the related art that the presence of rosemary extract in a composition containing capsicum would act to make the capsicum more tolerable to the user.

An embodiment of the present invention is a composition comprising an aqueous solution of capsicum at a concentration of about 0.00060% to about 0.010% w/w. An embodiment may comprise eucalyptol at a concentration of about 0.07% to about 0.15% w/w, wherein the composition is suitable for intranasal administration to a human in need thereof, wherein the first relief from at least one symptom occurs within about 30 minutes of administration, and wherein the symptoms consist of at least one of nasal congestion, sinus pressure, sinus pain, headache or a combination thereof. In an embodiment the eucalyptol may be at a concentration of about 0.13% w/w. In an embodiment the aqueous solution of capsicum comprises a homeopathic dilution of capsicum. In an embodiment the aqueous solution of capsicum may comprise a homeopathic dilution of Capsicum annum. In one embodiment, the aqueous solution of capsicum may be at a concentration of about 0.0020% to about 0.0080% w/w, or containing about 0.3 to about 1.5 ppm total capsaicinoids. In one embodiment, the aqueous solution of capsicum may be at a concentration of about 0.0030% to about 0.0080% w/w, or containing about 0.5 to about 1.5 ppm total capsaicinoids. In an embodiment the composition may also comprise rosemary extract at a concentration of about 0.02% to about 0.25% w/w, about 0.05% to about 0.10% w/w or comprise rosemary extract at a concentration of about 0.06% to about 0.07% w/w. In an embodiment the composition does not require the administration of a separate agent before, during, and/or after administration of the composition to enable tolerance of the composition. In an embodiment the composition is self-administered by the human in need thereof.

In an embodiment the composition may also comprise vegetable glycerin at a concentration of about 3.5% to about 5.0% w/w or at a concentration of about 3.9% to about 4.5% w/w. In an embodiment the composition may comprise ascorbic acid at a concentration of about 0.10% to about 0.90% w/w, sea salt at a concentration of about 0.40% to about 1.2% w/w, potassium sorbate at a concentration of about 0.05% to about 0.3%, or a combination thereof. In an embodiment the composition may provide the first relief from at least one symptom within about 30 minutes, 15 minutes, 5 minutes, 3 minutes, or within about 1 minute of administration.

An embodiment of the present invention is a composition comprising an aqueous solution of capsicum at a concentration of about 0.00060% to about 0.010% w/w, or containing about 0.1 to about 2.0 ppm total capsaicinoids and rosemary extract at a concentration of about 0.02% to about 0.25% w/w. An embodiment may further comprise eucalyptol at a concentration of about 0.07% to about 0.15%, vegetable glycerin at a concentration of about 3.5% to about 5.0% w/w or a combination thereof, wherein the composition is suitable for intranasal administration to a human in need thereof, wherein fast relief is first relief from at least one symptom occurring within about 30, 15, or 5 minutes of administration, wherein the symptoms consist of at least one of nasal congestion, sinus pressure, sinus pain, headache or a combination thereof. The composition may also comprise ascorbic acid at a concentration of about 0.10% to about 0.90% w/w, sea salt at a concentration of about 0.40% to about 1.2% w/w and potassium sorbate at a concentration of about 0.05 to about 0.3%, or a combination thereof. The composition may provide first relief from at least one symptom within about 3 minutes of administration or may provide first relief from at least one symptom within about 1 minute of administration.

An embodiment of the present invention is an aqueous solution suitable for intranasal administration to a human in need thereof, comprising an aqueous solution of capsicum at a concentration of about 0.00060% to about 0.010% w/w, or containing about 0.1 to about 2.0 ppm total capsaicinoids, rosemary extract at a concentration of about 0.02% to about 0.25% w/w, eucalyptol at a concentration of about 0.07% to about 0.15%, vegetable glycerin at a concentration of about 3.5% to about 5.0% w/w, or a combination thereof, wherein, on introduction into the nasal cavity of a human in need thereof, first relief from at least one symptom occurs within about 30, 15, or 5 minutes of administration, wherein symptoms comprise at least one of nasal congestion, sinus pressure, sinus pain, headache or a combination thereof. In an embodiment the aqueous solution of capsicum comprises a homeopathic dilution of capsicum. In an embodiment the aqueous solution of capsicum may be at a concentration of about 0.0020% to about 0.0080% w/w, or containing about 0.3 to about 1.5 ppm total capsaicinoids.

An embodiment of the present invention is a method for treating a human in need thereof comprising the steps of intranasal administration of an aqueous solution of capsicum and effecting the relief of at least one rhinitis symptom. The aqueous solution of capsicum may comprise a homeopathic dilution of capsicum, including, but not limited to, *Capsicum annum*. In an embodiment, the composition may comprise about 0.00060% to about 0.010% w/w capsicum, or containing about 0.1 to about 2.0 ppm total capsaicinoids, effecting the first relief from symptoms of at least one of nasal congestion, sinus pressure, sinus pain, headache or a combination thereof within about 30, 15, or 5 minutes of administration. In an embodiment the capsicum may be present in solution at a concentration of about 0.0020% to about 0.0080% w/w, or containing about 0.3 to about 1.5 ppm total capsaicinoids. In an embodiment the first relief from at least one symptom may occur within about 3 minutes or within about 1 minute of administration.

An embodiment of the present invention is a method for treating a human in need thereof comprising the steps of intranasal administration of an aqueous solution of capsicum comprising about 0.00060% to about 0.010% w/w capsicum, or containing about 0.1 to about 2.0 ppm total capsaicinoids, and rosemary extract at a concentration of about 0.02% to about 0.25% w/w, effecting the first relief from symptoms of at least one of nasal congestion, sinus pressure, sinus pain, headache or a combination thereof within about 30, 15, or 5 minutes of administration. In an embodiment the aqueous solution of capsicum may comprise a homeopathic dilution of capsicum, and may comprise a homeopathic dilution of *Capsicum annum*. In an embodiment the capsicum may be present in solution at a concentration of about 0.0020% to about 0.0080% w/w, or containing about 0.3 to about 1.5 ppm total capsaicinoids. In an embodiment the first relief from at least one symptom may occur within about 3 minutes of administration or within about 1 minute of administration.

An embodiment of the present invention is a method for treating a human in need thereof comprising the steps of intranasal administration of an aqueous solution of capsicum comprising about 0.00060% to about 0.010% w/w capsicum, or containing about 0.1 to about 2.0 ppm total capsaicinoids, and eucalyptol at a concentration of about 0.07% to about 0.15% w/w, effecting the first relief from symptoms of at least one of nasal congestion, sinus pressure, sinus pain, headache or a combination thereof within about 30, 15, or 5 minutes of administration. In an embodiment the aqueous solution of capsicum comprises a homeopathic dilution of capsicum. In an embodiment the capsicum may be present in solution at a concentration of about 0.0020% to about 0.0080% w/w, or containing about 0.3 to about 1.5 ppm total capsaicinoids. In an embodiment the first relief from at least one rhinitis symptom may occur within about 3 minutes of administration.

An advantage of an embodiment of the present invention is an intranasally administered composition having a quick and/or fast onset of action with an average time to first relief of at least one symptom of less than about thirty minutes, about fifteen minutes, about five minutes, about three minutes, and even less than about one minute.

An embodiment of the present invention is an intranasally administered composition that provides relief from at least one of nasal congestion, sinus pressure, sinus pain and headache with an improved therapeutic response that continues over time with at least one of nasal congestion, sinus pressure, sinus pain and headache significantly improved at about 5, 10, 15, 30 and/or 60 minutes. An advantage of an embodiment of the present invention is an intranasally administered composition having a rapid onset of action and significant reduction of symptoms that may be an attractive mono-therapy or adjunctive therapy for the management of rhinitis symptoms.

An embodiment of the present invention is an intranasal composition wherein users experience little to no rebound congestion. An advantage of an embodiment of the present invention is an intranasal composition wherein users experience essentially no alteration, or even an improvement, in olfaction versus placebo after continued use. An advantage of an embodiment of the present invention is a nasally administered composition that provides a rapid onset of relief for rhinitis subjects, while also providing safe, sustained relief over the course of a treatment period.

An advantage of an embodiment of the present invention is an intranasally administered composition wherein during a treatment period is significantly effective at improving at least one of nasal congestion, sinus pressure, sinus pain and headache compared to placebo.

An advantage of an embodiment of the present invention is an intranasally administered composition that is well-tolerated and with prolonged treatment results in substantially no reduction in olfaction.

An advantage of an embodiment of the present invention is an agent that may be used as a mono-therapy comprising capsaicin, dihydrocapsaicin, and nordihydrocapsaicin and other capsaicinoids.

In an embodiment of the present invention, the agent comprises between about 0.000001% to about 0.01% by weight of the total water or suspension material weight of capsicum comprising at least, but not limited to, capsaicin, dihydrocapsaicin, and nordihydrocapsaicin, resulting in about 0.0001 to about 1.5 ppm total capsaicinoids.

In another embodiment of the present invention the agent comprises between about 0.1 ppm to about 2.0 ppm total capsaicinoids comprising at least, but not limited to, capsaicin, dihydrocapsaicin, and nordihydrocapsaicin.

In another embodiment of the present invention, the agent comprises capsicum, comprising capsaicin, dihydrocapsaicin, and nordihydrocapsaicin, having a heat range of about 100,000 to about 1,000,000 Scoville Heat Units.

These and other embodiments of the present invention are more fully described in connection with the detailed description.

DETAILED DESCRIPTION OF THE INVENTION

Figure 1:
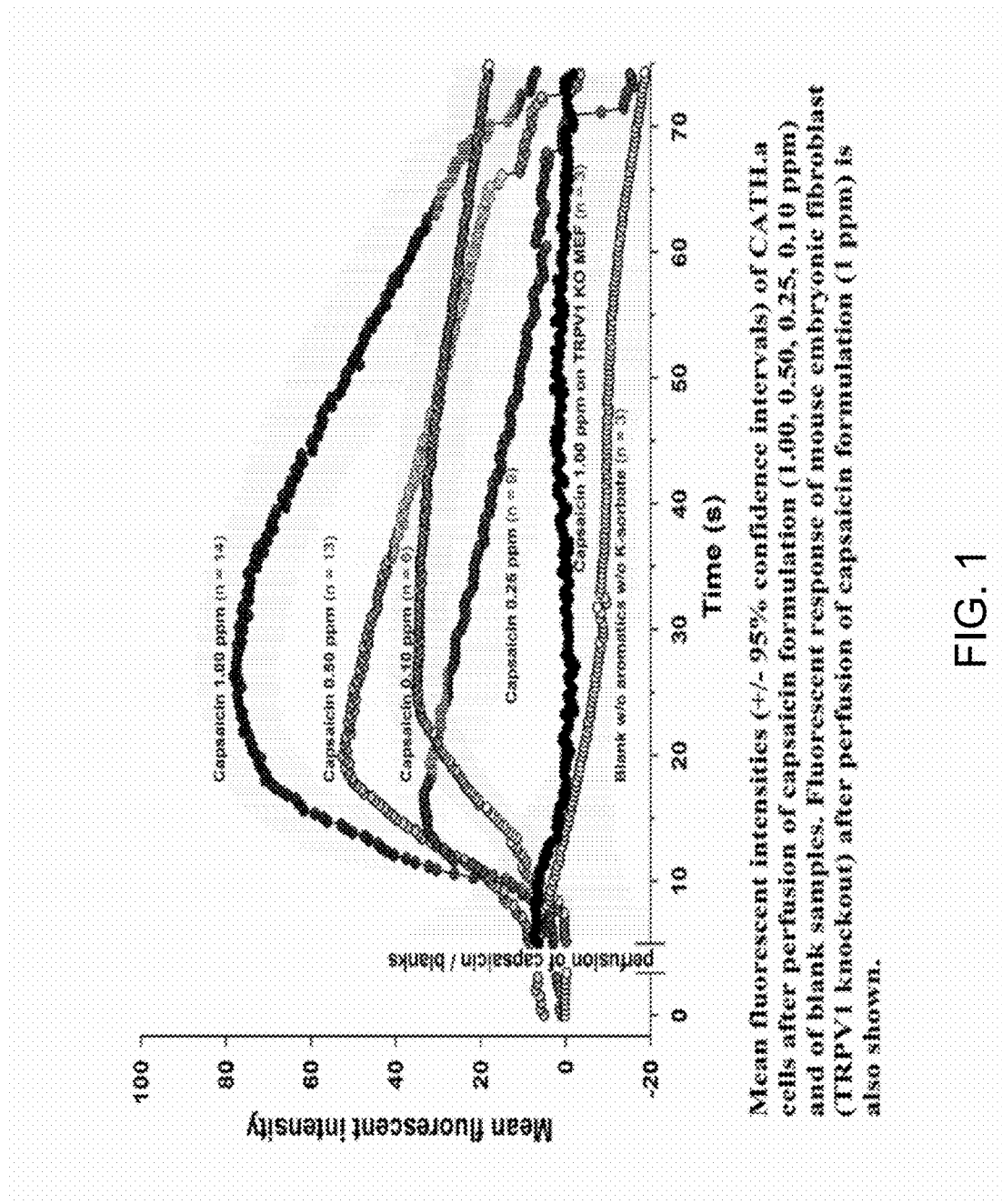
FIG. 1 is a diagram of the mean fluorescent intensity.

Capsicum is derived from several Capsicum pepper varieties. The Capsicum variety utilized in embodiments of the present invention is derived from cayenne pepper plants, which may comprise at least one of *Capsicum baccatum*, *Capsicum annum*, and *Capsicum frutescens*, or a combination thereof. The capsicum comprises capsaicin, dihydrocapsaicin, and nordihydrocapsaicin and possibly other capsaicinoids as active ingredients. The capsicum utilized in an embodiment of the present invention may comprise an all natural, water soluble and/or soluble liquid suspension material. The aqueous solution of capsicum may comprise a homeopathic dilution of capsicum. The aqueous solution of capsicum may comprise a homeopathic dilution of *Capsicum annum*. The use of capsicum comprising capsaicin, dihydrocapsaicin, nordihydrocapsaicin, and possibly other capsaicinoids as opposed to synthetic capsaicin may allow for repeated use and effective delivery without causing an uncomfortable and/or intolerable burning sensation in the nasal mucosa of the user. However, it is within the scope of the present invention that a combination of at least one synthetic capsaicinoid could also be used.

Embodiments of the present invention relate to an agent comprising capsicum comprising capsaicin, dihydrocapsaicin, nordihydrocapsaicin, and other capsaicinoids to relieve at least one rhinitis symptom in a human in need thereof. The aqueous solution of capsicum may comprise a homeopathic dilution of capsicum.

In an embodiment of the present invention, the composition may comprise between about 0.000001% to about 0.008% by weight of the total water or suspension material weight of capsicum comprising capsaicin, dihydrocapsaicin, and nordihydrocapsaicin among others, resulting in about 0.0001 to about 1.5 ppm total capsaicinoids.

In an embodiment of the present invention the composition comprises between about 0.1 to about 2.0 ppm total capsaicinoids present in capsicum, including, but not limited to, capsaicin, dihydrocapsaicin, and nordihydrocapsaicin.

In an embodiment of the present invention the composition may comprise capsicum including capsaicin, dihydrocapsaicin, and nordihydrocapsaicin and possibly other capsaicinoids having a heat range of between about 100,000 to about 1,000,000 Scoville Heat Units. The capsicum including, but not limited to, capsaicin, dihydrocapsaicin, and nordihydrocapsaicin is present in a non-caustic and safe amount.

In an embodiment the aqueous solution of capsicum comprises a homeopathic dilution of capsicum. In an embodiment the aqueous solution of capsicum comprises a homeopathic dilution of Capsicum annum.

An embodiment of the present invention comprises rosemary extract at a concentration of about 0.02% to about 0.50% w/w in addition to the capsicum. The composition may comprise rosemary extract at a concentration of about 0.05% to about 0.10% w/w, or at a concentration of about 0.06% to about 0.07% w/w.

A surprising and unexpected result according to an embodiment of the present invention is that the presence of the rosemary extract acts to increase the tolerability of the capsicum in the composition to the user.

Applicant is not aware of any disclosure, teaching, or suggestion in the art that the addition of rosemary extract in a composition containing capsicum would act to make the capsicum more tolerable to the user.

An embodiment of the present invention may comprise eucalyptol at a concentration of about 0.07% to about 0.15% w/w in addition to the capsicum.

An embodiment of the present invention may comprise at least one of vegetable glycerin at a concentration of about 3.5% to about 5.0% w/w, vegetable glycerin at a concentration of about 3.9% to about 4.5% w/w, ascorbic acid at a concentration of about 0.10% to about 0.90% w/w, sea salt at a concentration of about 0.40% to about 1.2% w/w, potassium sorbate at a concentration of about 0.05% to about 0.30% or a combination thereof, in addition to the capsicum.

In an embodiment of the present invention the composition may be an intranasal spray. In a further embodiment of the present invention, the composition may be an intranasal spray wherein the capsicum is released in a metered dose. In yet another embodiment of the present invention the composition may be an intranasal spray wherein the capsicum is released in a time released dose. In yet another embodiment of the present invention the composition may be disposed in, about and/or around a swab for intranasal delivery.

An embodiment of the invention relates to a method of treating a human in need thereof, by delivering the composition described herein and wherein capsicum including, but not limited to, capsaicin, dihydrocapsaicin, and nordihydrocapsaicin is the effective agent. The method comprises the intranasal administration of capsicum comprising, but not limited to, capsaicin, dihydrocapsaicin, and nordihydrocapsaicin effecting the relief of at least one rhinitis symptom. It will be apparent to one skilled in the art that the following are examples of formulations and many more formulations are possible and fall within embodiments of the present invention as disclosed and claimed herein.

EXAMPLE 1

It is hypothesized that capsicum, comprising capsaicinoids, including capsaicin, and possibly other ingredients in Applicant's composition, used for relief of rhinitis and allergic symptoms act via activation of TRP-family receptors. Applicant has developed an in vitro fluorometric assay to measure receptor activity in the presence of various concentrations of capsaicin/capsaicinoids. The activation of the receptors in the in vitro assay correlates with Applicant's demonstrated symptom relief as evidenced in the examples below. Specifically, the goal of the in vitro assay is to quantitatively measure TRPV activation to determine the dose response of airway component cells to Applicant's compositions comprising capsaicin/capsaicinoids. To this end, Applicant developed a new assay for transient receptor protein vanilloid ("TRPV") activation in cells. The assay is fluorometric in nature, relying upon a calcium-binding fluor, Fura-4. (available from Invitrogen Life Sciences and other vendors). Fura-4 fluoresces at a specific wavelength when it binds to calcium. Cells are loaded with Fura-4, and under digital confocal observation exposed to capsaicin/capsaicinoid containing compositions. The signal intensity over single cells is captured for 0.5-5 minutes and the result expressed as normalized (to baseline) signal intensity over time.

As shown in FIG. 1, the activation of a calcium channel by the composition will result in an increase in fluorescence. In the case of TRPV channels, since the channels are activated transiently (hence the name, Transient Receptor Potential V channels, TRPV,) the signals rapidly diminish in 1-2 minutes. The effects of the capsaicin/capsaicinoid-containing compositions to TRPV1 knockout cells (gene targeted ablation of the TRPV1, capsaicin receptor) is shown. Applicant performed the assay using compositions comprising varying levels of capsaicin/capsaicinoids, shown in FIG. 1, and achieved a dose-response, demonstrating that the in vitro assay distinguishes responses of about 1 ppm (n=14), 0.5 ppm (n=12), 0.25 ppm (n=8) and 0.10 ppm (n=4) concentration of total capsaicinoids, including capsaicin. The concentration at 1 ppm is about 0.0064% w/w capsicum, 0.5 ppm concentration is about 0.0032% w/w capsicum, 0.25 ppm concentration is about 0.0016% w/w capsicum, and the 0.10 ppm concentration is about 0.0008% capsicum. Responses are statistically different at the peak of activation ($P<0.05$). Mean (curves) and standard deviation (vertical lines) of fluorescent intensities of cells treated with the indicated compositions are shown. Formulations were perfused at time=0, and intensity plotted vs. time (seconds). Each signal was normalized to the baseline reading of that cell or part of a cell before infusion (to account for differential loading of Fura-4 and baseline differences in intracellular calcium levels). Applicant is not aware of any known in vitro studies that show the receptor response resulting from the administration of homeopathic doses of capsicum/capsaicinoid containing compositions.

In addition to the dose-response, the assay demonstrates that there is no calcium uptake in the blank sample (no aromatics, no capsaicinoids, n=1, Preliminary Data). Cells with gene targeted ablation of the TRPV1 channel ("TRPV1 KO") also show no increase in signal (n=1, Preliminary Data), supporting that the signal activated by the capsaicin/capsaicinoid containing formulations is indeed TRPV1-dependent. Applicant concludes from the data that the capsaicin response is primarily due to TRPV1, but expects that other TRPs will respond to the aromatics and the affect may be different in different cell types.

The results of this study indicate that a range of capsaicinoids from about 0.1 ppm to about 1 ppm total capsaicinoids significantly activates the TRPV channels over the controls. Applicant may easily extrapolate this data to reasonably infer and support a concentration range of capsaicin/capsaicinoids that will be effective at relieving rhinitis symptoms in humans in need thereof. Various formulations and concentrations of capsaicin/capsaicinoids have been used by Applicant to successfully treat these symptoms as shown in Examples 2-5 below. The following examples of formulations of compositions wherein the total capsaicinoids provide quick, effective relief from symptoms.

EXAMPLE 2

A clinical study was performed to assess the efficacy and safety of a newly formulated intranasally administered capsicum composition ("ICX") used continuously over a two week treatment period in chronic rhinitis subjects who have a significant component of NAR. The ICX formulation comprises from about 0.00060% to about 0.010% w/w, or comprising about 0.1 to about 2.0 ppm total capsaicinoids, about 0.0020% to about 0.0080% w/w, resulting in about 0.3 to about 1.5 ppm total capsaicinoids, or preferably about 0.0030% to about 0.0080% w/w, resulting in about 0.5 to about 1.5 ppm total capsaicinoids. The ICX formulation further comprises rosemary extract at a concentration of about 0.02% to about 0.25% w/w, eucalyptol at a concentration of about 0.07 to about 0.15%, vegetable glycerin at a concentration of about 3.5% to about 5.0% w/w, ascorbic acid at a concentration of about 0.10% to about 0.90% w/w and sea salt at a concentration of about 0.40% to about 1.2% w/w. One embodiment may also comprise potassium sorbate at a concentration of about 0.05% to about 0.30%. One embodiment of the ICX formulation comprises about 0.0064% w/w capsicum, about 0.11% w/w eucalyptol, about 0.067% w/w rosemary extract, about 0.4 to about 0.7% w/w each ascorbic acid and sea salt, about 4.4% w/w vegetable glycerin, in purified water.

Figure 4:
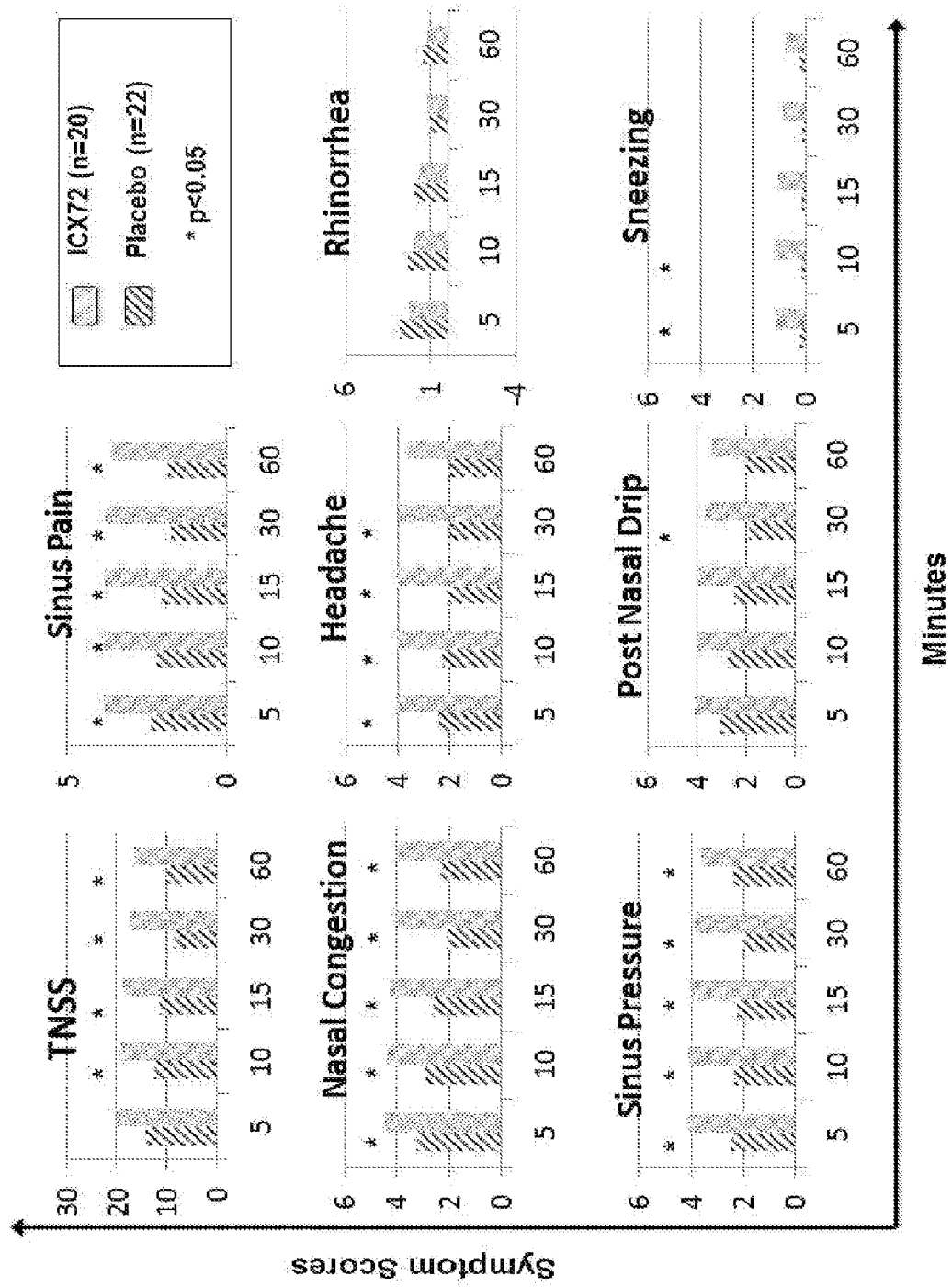
FIG. 4 is a diagram of symptom scores of ICX72 and a placebo.

Forty-two informed, consented patients with a significant component of NAR were randomized to receive either ICX (n=20) or a filtered water control (n=22), as shown in FIG. 4, administered 1-2 puffs in each nostril twice daily over 2 weeks. The primary endpoint was change in total nasal symptom scores ("TNSS") from baseline to end of study. Secondary endpoints included changes in individual symptom scores (nasal congestion, sinus pain, sinus pressure, headache, sneezing, rhinorrhea, and post-nasal drainage) over two weeks and average time to first relief. Mean TNSS and individual symptom scores were also recorded after single dosing with ICX vs. placebo at 5, 10, 15, and 60 minute intervals. Rhinitis quality-of-life domains at end of study, and use of rescue medication and safety endpoints were also analyzed. All data was analyzed by the Statistical Analysis System ("SAS").

Statistically significant differences in changes from baseline to end of study between the ICX and placebo groups were observed for TNSS and each individual symptom (p<0.01). The average time to first relief for ICX subjects was 52.6 seconds which was significantly less than placebo (p<0.01). For ICX subjects, nasal congestion, sinus pain, sinus pressure and headache were significantly improved at 5, 10, 15, 30, which persisted up until 60 minutes for nasal congestion and sinus pain (p<0.05). No significant difference between groups in adverse events or rescue medication was observed. ICX subjects experienced no rebound congestion and demonstrated an improvement in olfaction versus placebo at the end of study visit.

This is the first controlled clinical trial to demonstrate that the ICX composition comprising capsicum provides a rapid onset of relief for rhinitis subjects, while also providing safe, sustained relief over the course of the two week treatment period.

This was a randomized, placebo controlled, double-blind parallel study including patients previously diagnosed with non-allergic rhinitis ("NAR") or "mixed rhinitis" defined as allergic rhinitis ("AR") with significant NAR triggers. (Bernstein J A. Characteristics of Non-Allergic Rhintiis. World Allergy Journal 2009; 2:102-5. Bernstein J A, Rezvani, M. Mixed Rhinitis: A New Subclass of Chronic Rhinitis. In: Kaliner M, ed. Current Review of Rhinitis, 2nd ed 2006; Philadelphia, Pa.:69-78

Forty-two patients between the ages of 18-60 were enrolled in this study. All subjects signed an informed consent approved by a central IRB prior to enrollment. Subjects were required to have a diagnosis of NAR with or without an allergic component (i.e. mixed rhinitis) for at least six months prior to enrollment. Mixed rhinitis was defined as being skin prick test positive, defined as a wheal ≥3 mm in diameter than saline control with surrounding erythema, to one or more aeroallergens in addition to having significant symptoms induced by chemical irritants, strong odors, weather or temperature changes. (Bernstein J A, Rezvani, M. Mixed Rhinitis: A New Subclass of Chronic Rhinitis. In: Kaliner M, ed. Current Review of Rhinitis, 2nd ed 2006; Philadelphia, Pa.: 69-78.) The magnitude of each subject's non-allergic rhinitis component was confirmed using a gender specific irritant index score previously demonstrated to correlate with a diagnosis of NAR or MR. (Bernstein J A. Characteristics of Non-Allergic Rhintiis. World Allergy Journal 2009; 2:102-5.) Twenty subjects received ICX and 22 received placebo control (filtered water). Thirty-three of the 42 participants had a diagnosis of MR, and 9 had an NAR diagnosis. These diagnoses were evenly distributed between the ICX and placebo groups. All subjects enrolled into this study and randomized to ICX or placebo control and who received at least one dose of study drug were included in this intent-to-treat analysis.

All subjects were required to have previously experienced symptomatic relief while using their currently prescribed rhinitis medications and were required to exhibit moderate to severe rhinitis symptoms while off these medications at the time of randomization. Symptom severity was defined as a morning or evening nasal congestion and/or post nasal drainage score of at least 5 out of 10 on three separate symptom assessments during the 7 day pre-randomization medication wash-out period. This included being symptomatic at least 24 hours prior to and including the day of randomization. Subjects were required to comply with all study related visits and procedures and had to be in generally good health without any uncontrolled chronic health problems.

Subjects were excluded if they had an acute sinus infection in the past 30 days, had a history of nasal polyps or other nasal structural problems, were treated with oral corticosteroids in the past 7 days, were active smokers or had passive smoke exposure at least six months prior to enrollment. Finally, pregnant women were not permitted to participate and women of child bearing age were required to use acceptable birth control throughout the study.

Figure 2:
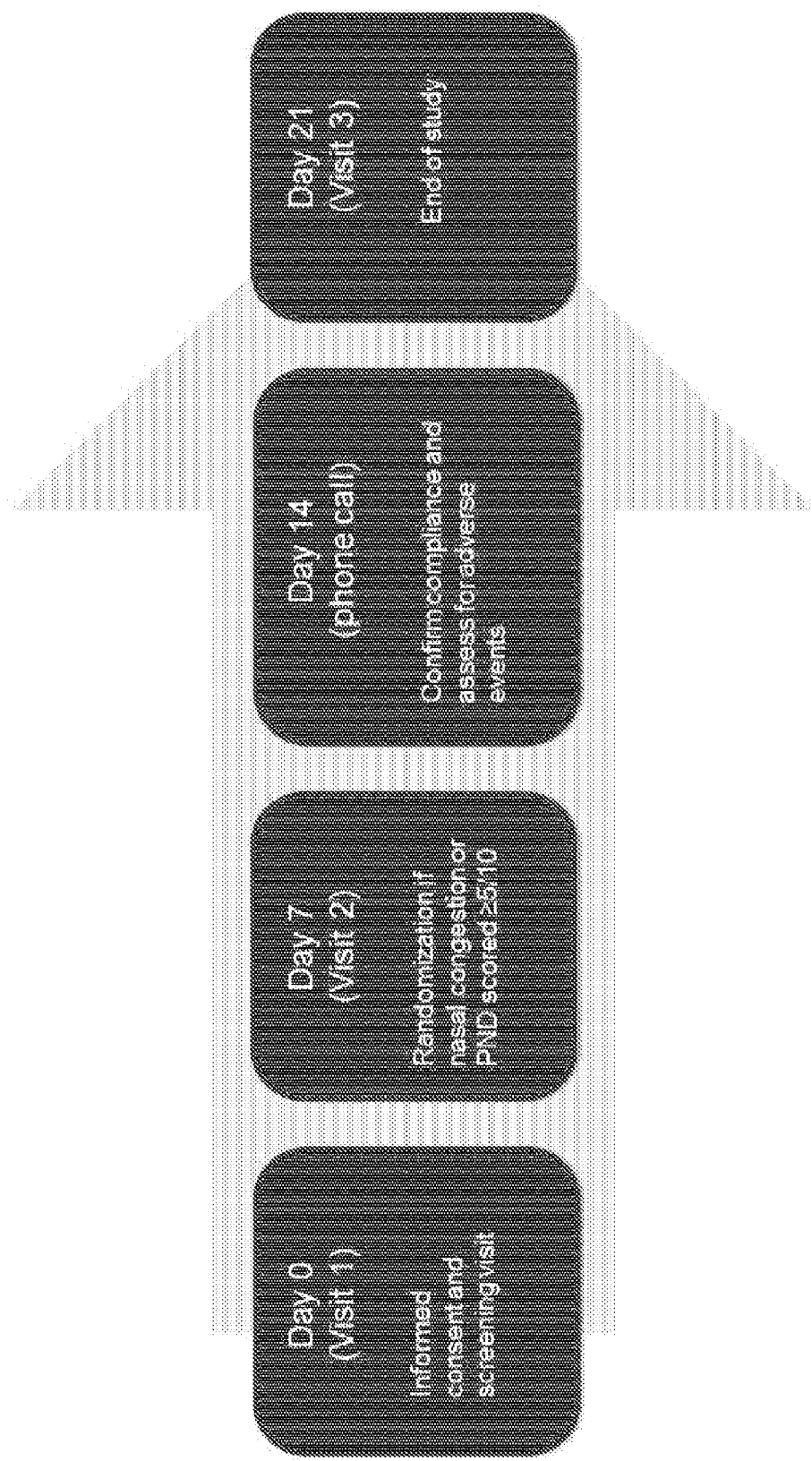
FIG. 2 is a diagram of a schedule of the study protocol.

There were a total of three study visits and one interim phone call, as shown in FIG. 2.

During visit one, subjects who signed an informed consent and met all inclusion/exclusion criteria (except for symptom scores), were removed from all rhinitis medications for 7 days to determine if they would fulfill the symptom entry criteria. They were permitted to use diphenhydramine 25 mg up to 200 mg/day as rescue medication throughout the study. During visit two, subjects who fulfilled all inclusion/exclusion criteria including the symptom score criteria, were randomized to receive either ICX or filtered water placebo, 1-2 puffs each nostril, twice daily. During visit 2, subjects were given their first dose of study drug or placebo in the office. Using the stopwatch method, subjects clicked the stopwatch when they felt the first onset of symptom relief. (Black P, Max M B, Desjardins P, Norwood T, Ardia A, Pallotta T. A randomized, double-blind, placebo-controlled comparison of the analgesic efficacy, onset of action, and tolerability of ibuprofen arginate and ibuprofen in postoperative dental pain. Clin Ther 2002; 24:1072-89.) They were then immediately instructed to complete a symptom score card. Subjects also completed symptom score cards at 5, 10, 15, 30 and 60 minute intervals during this visit.

An interim phone call to the subject's home was made 7 days later to confirm compliance with completing home symptom diaries and to assess for adverse events and rescue medication requirements. The study ended at visit three, two weeks after randomization (visit 2).

During each visit, all subjects had a directed medical history, nasal examination, and a review of concomitant and/or rescue medications. During visits 1 and 3, all subjects underwent acoustic rhinometry and automated olfactometry to assess nasal congestion and smell, respectively. (Bernstein J A, Bernstein I L. A novel case of mealworm-induced occupational rhinitis in a school teacher. Allergy Asthma Proc 2002; 23:41-4. Rezvani M, Brandt D, Bernstein J A, Hastings L, Willwerth J. Investigation of olfactory threshold responses in chronic rhinitis subtypes. Ann Allergy Asthma Immunol 2007; 99:571-2.) Pregnancy tests were performed on all women of child bearing age at visits 1 (screening) and 2 (randomization). Rescue medication and adverse events were assessed at visit 2, during the interim phone call, and at visit 3.

Symptom scores and rescue medication requirements, consisting of diphenhydramine 25-50 mg up to four times a day (maximum dose 200 mg/day), were recorded on subject's home diaries over the three week study period.

The primary endpoint was the change in the 12 hour reflective total TNSS recorded by the patient each evening in a daily diary, from baseline to the end of the study (2 weeks). TNSS was a composite score that included nasal congestion, postnasal drainage, sneezing, rhinorrhea, sinus pain, sinus pressure and headache. These symptoms were chosen based on the "Allergies in America survey" which cited these as the worst symptoms and/or co-morbid conditions experienced by chronic rhinitis patients. (Blaiss M S, Meltzer E O, Derebery M J, Boyle J M. Patient and healthcare-provider perspectives on the burden of allergic rhinitis. Allergy Asthma Proc 2007; 28 Suppl 1:S4-10.) Each symptom was rated on a 10 point Likert scale and therefore, the highest possible TNSS was 70, where a higher score reflects more intense symptoms.

Secondary endpoints included changes in 12 hour reflective symptom scores of nasal congestion, post-nasal drainage, sneezing, rhinorrhea, sinus pain, sinus pressure and headache recorded at home daily by patients on diary cards over a 2-week period and the time to first relief of symptoms recorded in the physician office at visit 2, after single dosing with ICX or placebo.

Other endpoints included changes in symptom scores (TNSS, nasal congestion, post-nasal drainage, sneezing, rhinorrhea, sinus pain, sinus pressure and headache) at the time to first relief and assessment of rescue medication requirements during the entire 2 week study period.

Adverse events, olfaction as measured using an automated olfactometer (Osmic Enterprises, LLC) (Rezvani M, Brandt D, Bernstein J A, Hastings L, Willwerth J. Investigation of olfactory threshold responses in chronic rhinitis subtypes. Ann Allergy Asthma Immunol 2007; 99:571-2), and nasal congestion using an acoustic rhinometer (Ecco Vision, Hood Instruments, Pembroke, Mass.) to assess for increased nasal resistance (i.e., a rebound effect) (Bernstein J A, Bernstein I L. A novel case of mealworm-induced occupational rhinitis in a school teacher. Allergy Asthma Proc 2002; 23:41-4) were recorded and assessed prior to randomization while off all rhinitis medications and at the end of study.

The sample sizes for the ICX drug and placebo control groups were chosen based on feasibility and other intranasal capsaicin studies that reported clinically meaningful results. (Blom H M, Van Rijswijk J B, Garrelds I M, Mulder P G, Timmermans T, Gerth van Wijk R. Intranasal capsaicin is efficacious in non-allergic, non-infectious perennial rhinitis. A placebo-controlled study. Clin Exp Allergy 1997; 27:796-801.) For sample sizes of 20 per group, the power was 80% to detect a difference of 2 units in TNSS mean scores from baseline to 14 days between the drug and placebo groups assuming a 2-tailed alpha=0.05. The effect size (ratio of mean difference to TNSS standard deviation) was equal to 0.8.

For all analyses a p-value <0.05 was used to judge statistical significance unless stated otherwise. The analyses were performed using SAS for Windows, version 9.2, SAS Institute, Cary N.C.

Subject demographics: The demographic characteristics of the subject population are summarized in Table 1.

TABLE 1

Demographic Characteristics of Study Participants

|  | Capsaicin (N = 20) | Placebo (N = 22) | All (N = 42) |
|---|---|---|---|
| AGE, mean (min, max) | 46.9 (36, 59) | 45.2 (29, 58) | 46.0 (29, 59) |
| RACE, N (%) |  |  |  |
| Caucasian | 17 (85%) | 17 (77%) | 34 (81%) |
| African American | 2 (10%) | 5 (23%) | 7 (17%) |
| Other | 1 (5%) | 0 (0%) | 1 (2%) |
| GENDER, N (%) |  |  |  |
| Male | 4 (20%) | 3 (14%) | 7 (17%) |
| Female | 16 (80%) | 19 (86%) | 35 (83%) |

Note:
No significant differences were seen between the ICX72 and placebo groups (p > .05).

There were no significant differences between subjects in the ICX and placebo groups with respect to age, race and gender.

Mean Changes in TNSS and Individual Symptom Scores from Baseline to End of Study for ICX and Placebo Groups: Mean baseline symptom scores of the ICX and placebo groups were not significantly different as shown in Table 2.

TABLE 2

Mean Change from Baseline to End of Study (Standard Error) of TNSS and Individual Symptom Scores for ICX72 and Placebo Groups

|  | ICX72 (N = 20) | | | Placebo (N = 22) | | |
|---|---|---|---|---|---|---|
| Symptom | Baseline | Change: Baseline-End | % Rel Change | Baseline | Change: Baseline-End | % Rel Change |
| TNSS* | 23.7 (2.2) | 12.4 (1.1) | 52% | 26.0 (2.2) | 7.7 (1.2) | 30% |
| Nasal Congestion | 5.1 (0.5) | 2.7 (0.3) | 53% | 5.3 (0.4) | 1.4 (0.3) | 27% |
| Sinus Pressure | 5.4 (0.5) | 3.3 (0.3) | 62% | 3.7 (0.4) | 1.5 (0.3) | 29% |
| Sinus Pain | 4.5 (0.5) | 2.8 (0.3) | 64% | 4.8 (0.5) | 1.6 (0.3) | 33% |
| Headache | 4.9 (0.5) | 3.2 (0.4) | 65% | 4.8 (0.5) | 1.8 (0.3) | 37% |
| Sneezing | 1.6 (0.4) | 0.9 (0.2) | 53% | 2.4 (0.4) | 0.8 (0.2) | 19% |
| Rhinorrhea | 2.6 (0.5) | 0.5 (0.3) | 19% | 2.6 (0.4) | 0.6 (0.3) | 24% |
| PND | 4.7 (0.5) | 2.2 (0.4) | 47% | 5.6 (0.5) | 1.7 (0.3) | 30% |

Note:
For each variable, baseline differences between groups were not statistically different (p > 0.05). Percent relative change of each symptom was larger for ICX72, compared with placebo, except rhinorrhea. Mean changes from baseline to end of study were significantly different between ICX72 and placebo for TNSS, nasal congestion, sinus pressure, sinus pain and headache (p < 0.006 for each variable determined by Bonferroni adjustment, overall p-value = 0.05).

Figure 3:
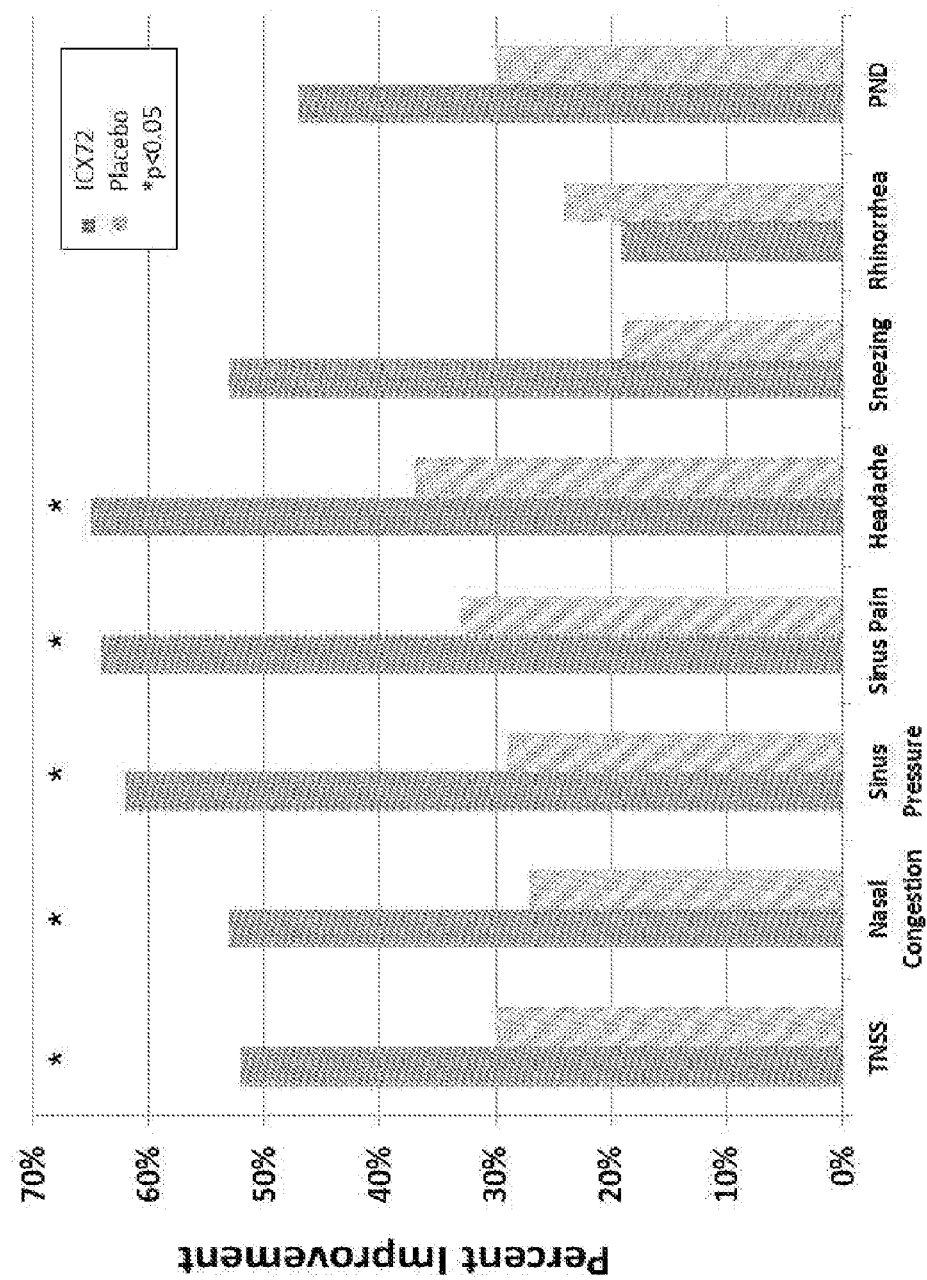
FIG. 3 is a diagram of the magnitude of improvement for TNSS.

The mean differences between the ICX and placebo groups with respect to changes in TNSS, nasal congestion, sinus pressure, sinus pain and headache from baseline to end of study were statistically greater for ICX compared to placebo (p<0.01). FIG. 3 illustrates the magnitude of this effect for TNSS and the individual symptoms that significantly improved. No significant differences between groups in changes from baseline to end of study were observed for sneezing, post-nasal drip and rhinorrhea (p>0.05).

Times to first relief: The average time to first relief for ICX was equal to 52.6 seconds (0.8 min), which was significantly lower than the average time of first relief for placebo subjects (p<0.01). Eighty percent of subjects receiving ICX experienced first relief in less than one minute compared to 45% of subjects receiving placebo (p<0.05). Symptoms that significantly improved at time to first relief were nasal congestion, sinus pressure and headache (p<0.05) as shown in Table 3.

TABLE 3

Mean Change from Baseline to First Relief (Standard Error) of
TNSS and Individual Symptom Scores for ICX72 and Placebo Groups

| | ICX72 (N = 20) | | | Placebo (N = 22) [a] | | |
|---|---|---|---|---|---|---|
| Symptom | Baseline | Change: Baseline-First Relief | % Rel Change | Baseline | Change: Baseline-First Relief | % Rel Change |
| TNSS | 23.7 (2.2) | 3.4 (1.5) | 14% | 26.0 (2.2) | 2.3 (7.7) | 9% |
| Nasal Congestion | 5.1 (0.5) | 1.3 (0.4) | 25% | 5.3 (0.4) | 0 (2.2) | 0% |
| Sinus Pressure | 5.4 (0.5) | 1.7 (0.5) | 32% | 3.7 (0.4) | −0.1 (1.9) | −1% |
| Sinus Pain | 4.5 (0.5) | 1.2 (0.6) | 27% | 4.8 (0.5) | −0.2 (2.7) | −5% |
| Headache | 4.9 (0.5) | 2.2 (0.6) | 44% | 4.8 (0.5) | −0.1 (2.0) | −2% |
| Sneezing | 1.6 (0.4) | 1.2 (0.3) | 75.0% | 2.4 (0.4) | 0.5 (1.8) | 19% |
| Rhinorrhea | 2.6 (0.5) | −2.3 (0.6) | −89% | 2.6 (0.4) | −1.9 (4.3) | −74% |
| PND | 4.7 (0.5) | 0.4 (0.7) | 7% | 5.6 (0.5) | −0.6 (5.4) | −10% |

[a] N=22 placebo patients at baseline = 22. Four patients had missing data at first relief for each symptom. When a symptom at first relief was missing, less relief was assumed than was determined from all reported symptom changes at first relief, after adjusting for baseline. The minimum values at first relief of missing data were symptom-specific. Mean symptom changes in the placebo group were obtained from Tobit analysis, which accounts for the upward bias of changes calculated from observed data only. The probability of unreported symptoms reflecting less relief than the minimum relief of all other patients was combined with the probabilities of the observed symptom values at first relief, to estimate mean changes at first relief of each symptom for the placebo group.

Note:
For each variable, baseline differences between groups were not statistically different ($p > 0.05$). Mean changes from baseline to first relief were significantly different between ICX72 and placebo for sinus pressure and headache only ($p < 0.006$ for each variable determined by Bonferroni adjustment, overall p-value = 0.05).

Improvement in TNSS and Symptoms Scores for Intranasal Capsaicin Compared to Placebo At Fixed Time Periods: This analysis required subjects to complete symptom score questionnaires at fixed time periods beginning at 5 minutes up to 60 minutes after the first dose. Differences were statistically significant for nasal congestion, sinus pressure, sinus pain and headache at 5, 10, 15 and 30 minutes which persisted for nasal congestion, sinus pressure and sinus pain up to 60 minutes ($p<0.05$).

Rescue medications: Fewer subjects in the ICX group (n=6; 30% of subjects) compared to the placebo group (n=10; 45% of subjects), reported rescue medication usage during the first week after randomization.

Similarly, fewer subjects in the ICX group (n=4; 20% of subjects) versus the placebo group (n=10; 45%) reported use of rescue medications during the second week after randomization.

Safety Analyses:

Olfactometry: The olfactory threshold means of ICX and placebo subjects at baseline and end of study are summarized in Table 4.

TABLE 4

Mean Change from Baseline to End of Study (Standard Error)
of Olfactory Thresholds for ICX72 and Placebo Groups.

| | ICX72 (N = 14) | | Placebo (N = 17) | |
|---|---|---|---|---|
| | Baseline | Change: Baseline-End | Baseline | Change: Baseline-End |
| Olfactory Threshold | 6.7 (0.4) | −1.0 (0.6) | 6.1 (0.6) | +0.1 (0.5) |

N = number of patients
A negative change (higher value at end of study) indicates improved olfaction. Baseline (defined as data collected during visit 2 pre-drug) differences between groups were not significantly different ($p > .05$). Mean changes from baseline to end of study were not significantly different between ICX72 and placebo groups ($p > .05$). End of study means were significantly different between ICX72 (7.7) and placebo (6.0) ($p < .05$).

There were no significant differences between baseline or the change from baseline to end of study olfactory threshold means for ICX and placebo subjects ($p>0.05$). However, ICX subjects, had significantly higher olfactory threshold means compared to placebo at visit 3 ($p<0.05$) indicating that their sense of smell was actually improved during the end of study visit compared to placebo.

Acoustic Rhinometry: There was no significant difference in nasal mean cross sectional areas or volumes at baseline (when subjects were removed from rhinitis medications) compared to end of study between ICX and placebo subjects (data not shown). This indicates that increased nasal resistance, which is what would be seen with rebound nasal congestion, was not a side effect when ICX was used continuously over 2 weeks.

Adverse Events: There was no significant difference between ICX and placebo in reported adverse events. Reported adverse events included increased nasal congestion, headaches, post-nasal drainage, rhinorrhea, transient stinging/burning, blood tinged mucus and fatigue. Ten percent of subjects on ICX and 27% on placebo, respectively ($p=0.24$) reported adverse events during the first week after randomization whereas, 45% of subjects on ICX and 32% on placebo ($p=0.53$) reported adverse events during the second week after randomization.

The results of this study clearly demonstrate that continuous treatment with ICX over a two week period was significantly effective at improving TNSS, nasal congestion, sinus pressure, sinus pain and headache compared to placebo. Furthermore, ICX has a quick onset of action as the average time to first relief was less than one minute (52.6 seconds). This rapid improvement was most pronounced for nasal congestion, sinus pressure and sinus pain.

Interestingly, this improved therapeutic response continued over time as nasal congestion, sinus pressure, sinus pain and headache were significantly improved for ICX versus placebo at 5, 10, 15 and 30 minutes and persisted for nasal congestion and sinus pain up until 60 minutes. Thus, the rapid onset of action resulting in significant reduction of symptoms makes ICX an attractive mono-therapy or adjunctive therapy for the management of chronic rhinitis symptoms.

Prolonged treatment with ICX resulted in no alteration in olfaction and in fact appeared to improve olfaction in patients receiving ICX versus placebo at end of study. Furthermore, subjects receiving ICX continuously over two weeks showed no rebound congestion as reflected by improved symptom scores and no change in nasal cross sectional area measured by acoustic rhinometry. Other than a transient stinging sensation, ICX was well tolerated.

Several important points regarding this study should be emphasized. First, this is the first study to demonstrate that continuous daily treatment with a composition comprising a lower concentration of intranasal capsicum (ICX) over a two week period is safe and effective at improving chronic rhinitis symptoms. Second, in that all subjects in this trial were required to have a significant component of NAR as part of their enrollment criteria, the beneficial effect of ICX supports an important mechanistic role for TRP ion channels, specifically TRPV1 in NAR.

The robust effect of ICX on improving rhinitis symptoms and headaches suggest overlapping neurogenic mechanistic pathways for MR, NAR and headaches, perhaps in part involving TRP ion channels, that require further investigation. (Rapoport A M, Bigal M E, Tepper S J, Sheftell F D. Intranasal medications for the treatment of migraine and cluster headache. CNS Drugs 2004; 18:671-85.)

There are several potential limitations of this study that warrant discussion. First, similar to what has been encountered for other intranasal medications (Banov C H, Lieberman P. Efficacy of azelastine nasal spray in the treatment of vasomotor (perennial nonallergic) rhinitis. Ann Allergy Asthma Immunol 2001; 86:28-35.), it was not possible to formulate a placebo that caused mild transient stinging similar to the ICX formulation used in this trial. However, in order to ensure that the study remained blinded to the subject, both the clinical research coordinator and investigator used common written instructions to direct the patient through different procedures thereby limiting any unnecessary conversations during the study visits that could bias the subject or coordinator. Second, it is worth noting that subjects receiving placebo in some instances experienced modest improvement in TNSS and specific symptom scores compared to baseline. The therapeutic effect of placebo in clinical trials has been well established. (Spector S L. The placebo effect is nothing to sneeze at. J Allergy Clin Immunol 1992; 90:1042-3.) However, the finding that ICX had a faster onset of action and greater overall improvement in nasal congestion and TNSS compared to a placebo control at various time points throughout the study is a testimonial to its robust therapeutic benefits.

In summary, this is the first controlled clinical trial to demonstrate that ICX provides a rapid onset of relief for rhinitis subjects with a non-allergic component, while also providing safe, sustained relief over the course of the two week treatment period.

EXAMPLE 3

One example of the present invention relates to a headache relief composition. The headache relief composition provides relief of symptoms such as migraines, general headaches, tension, chronic and occasional headaches, and dizziness, and visual distortions associated with headaches. The headache relief composition comprises capsicum comprising capsaicin, dihydrocapsaicin, and nordihydrocapsaicin, feverfew extract, eucalyptol, peppermint oil, rosemary extract, vegetable glycerin, ascorbic acid, citric acid, and sea salt. An embodiment may comprise potassium sorbate at a concentration of about 0.05% to about 0.30% w/w.

The feverfew extract relieves and prevents headache symptoms. The eucalyptol is used to ameliorate the sensory experience and soothe the nasal mucosa. The peppermint oil relieves and helps prevent headache symptoms. The rosemary extract is an anti-microbial agent and a natural preservative which protects and stabilizes the headache relief composition. In a surprising and unexpected result, the rosemary extract was also found to make the sensory experience due to the presence of capsicum in the composition more tolerable to the user, without negatively affecting the efficacy of the composition. The vegetable glycerin is a moisturizer, assists the capsaicinoids contained in the capsicum to maintain its potency and effectiveness for longer periods of time, shortens the length of time of the burning sensation associated with the capsaicinoids in the capsicum without reducing its effectiveness, and stabilizes the formula. The ascorbic acid adjusts the pH supports the immune system, and acts as a natural preservative. The citric acid further adjusts the pH level and stabilizes the formula. Any other suitable pH modulator may be used to adjust and/or maintain the pH of the composition. The sea salt acts as a nasal cavity cleanser which helps flush out bacteria, and dried or clogged mucous which can affect the performance of nerve receptors in the trigeminal region.

In another embodiment of the present invention, the headache relief composition may be homeopathic wherein the eucalyptol is used to ameliorate the sensory experience and soothe the nasal mucosa, and the feverfew extract is for headache relief. Furthermore, the headache relief composition may include both eucalyptol and feverfew extract as a tincture.

In still another embodiment of the present invention, the headache relief composition may include between about 0.0044% to 0.0047% by weight of the total water weight of capsicum comprising, but not limited to, capsaicin, dihydrocapsaicin, and nordihydrocapsaicin, or about 0.7 to about 1.5 ppm total capsaicinoids.

One example of the headache relief composition in accordance with an embodiment of the present invention in 5 gallons of purified water includes:

0.0044% to 0.0047% by weight of the total water weight of capsicum;
0.10% by weight of the total water weight of feverfew extract;
0.0027% by weight of the total water weight of peppermint oil;
0.13% by weight of the total water weight of eucalyptol;
0.08% by weight of the total water weight of rosemary extract;
3.65% by weight of the total water weight of vegetable glycerin;
0.53% by weight of the total water weight of sea salt;
0.83% by weight of the total water weight of ascorbic acid;
0.26% by weight of the total water weight of citric acid.

In another embodiment, the headache relief composition may be administered as a preventative and symptomatic tool. In one embodiment the composition may further comprise from about 0.05% to about 0.30% w/w or about 0.12% by weight of the total water weight of potassium sorbate.

EXAMPLE 4

Another example of the present invention relates to an allergy relief composition. The allergy relief composition provides relief of symptoms caused by allergies such as nasal congestion, sinus pressure, and headaches. The allergy relief composition includes capsicum comprising capsaicin, dihydrocapsaicin, and nordihydrocapsaicin, nettle extract, eucalyptol, rosemary extract, vegetable glycerin, ascorbic acid, citric acid, and sea salt.

The nettle extract helps relieve and desensitize allergy symptoms and related allergy triggers. The eucalyptol is used to ameliorate the sensory experience and soothe the nasal mucosa. The rosemary extract is an anti-microbial agent and a natural preservative which protects and stabilizes the allergy relief composition. In a surprising and unexpected result, the rosemary extract was also found to make the sensory experience due to the presence of capsicum in the composition more tolerable to the user, without negatively affecting the efficacy of the composition. The vegetable glycerin is a moisturizer, assists the capsaicinoids contained in the capsicum to maintain their potency and effectiveness for longer periods of time, shortens the length of time of the burning sensation associated with the capsaicinoids in the capsicum without reducing its effectiveness, and stabilizes the formula. The ascorbic acid adjusts the pH level, supports the immune system, and acts as a natural preservative. The citric acid adjusts the pH level and stabilizes the formula. Any other suitable pH modulator may be used to adjust and/or maintain the pH of the composition. The sea salt acts as a nasal cavity cleanser which helps flush out bacteria, and dried or clogged mucous therefrom. The potassium sorbate may be used as a preservative.

In another embodiment of the present invention, the allergy relief composition may be homeopathic wherein the eucalyptol is used to ameliorate the sensory experience and soothe the nasal mucosa. Furthermore, the homeopathic allergy relief composition may include eucalyptol as a tincture and nettle extract as a tincture.

In still another embodiment of the present invention, the allergy relief composition may include between about 0.0029% to 0.0032% by weight of the total water weight of capsicum comprising capsaicin, dihydrocapsaicin, and nor-dihydrocapsaicin, providing about 0.4 to about 0.5 ppm total capsaicinoids.

Another embodiment of the allergy relief composition in 5 gallons of purified water includes:
  0.0029% to 0.0032% by weight of the total water weight of capsicum;
  0.10% by weight of the total water weight of nettle extract;
  0.13% by weight of the total water weight of eucalyptol;
  0.08% by weight of the total water weight of rosemary extract;
  3.65% by weight of the total water weight of vegetable glycerin;
  0.53% by weight of the total water weight of sea salt;
  0.83% by weight of the total water weight of ascorbic acid; and
  0.26% by weight of the total water weight of citric acid.

In another embodiment, the allergy relief composition may be administered as a preventative and symptomatic tool. In an embodiment, the composition may further comprise potassium sorbate at a concentration of about 0.05% to about 0.30% w/w.

EXAMPLE 5

Another example of the present invention relates to a cold relief composition. The cold relief composition prevents and provides relief of symptoms caused by colds, flu, and poor immune system performance. The cold relief composition comprises capsicum including, but not limited to, capsaicin, dihydrocapsaicin, and nordihydrocapsaicin, echinacea extract, eucalyptol, golden seal extract, spearmint oil, vegetable glycerin, ascorbic acid, citric acid and sea salt.

The echinacea extract and the golden seal extract support the immune system. The eucalyptol is used to ameliorate the sensory experience and soothe the nasal mucosa. The spearmint oil provides a sweet taste. The vegetable glycerin is a moisturizer, assists the capsaicinoids contained in the capsicum to maintain its potency and effectiveness for longer periods of time, shortens the length of time of the burning sensation associated with the capsaicinoids in the capsicum without reducing its effectiveness, and stabilizes the formula. The ascorbic acid adjusts the pH level, supports the immune system, and acts as a natural preservative. The citric acid adjusts the pH level and stabilizes the formula. Any other suitable pH modulator may be used to adjust and/or maintain the pH of the composition. The sea salt acts as a natural preservative.

In another embodiment of the present invention, the cold relief composition may be homeopathic wherein the eucalyptol is used to ameliorate the sensory experience and soothe the nasal mucosa, and the echinacea extract and golden seal extract provide immune system support. Furthermore, the homeopathic cold relief composition may include eucalyptol as a tincture, echinacea extract as a tincture, and golden seal extract as a tincture.

In still another embodiment of the present invention, the cold relief composition may comprise between about 0.0024% to 0.0027% by weight of the total water weight of capsicum comprising capsaicin, dihydrocapsaicin, and nor-dihydrocapsaicin, providing about 0.3 to about 0.7 ppm total capsaicinoids.

One example of the cold relief composition in accordance with an embodiment of the present invention in 5 gallons of purified water includes:
  0.0024% to 0.0027% by weight of the total water weight of capsicum;
  0.20% by weight of the total water weight of echinacea extract;
  0.13% by weight of the total water weight of eucalyptol;
  0.15% by weight of the total water weight of golden seal extract;
  0.013% by weight of the total water weight of spearmint oil;
  0.53% by weight of the total water weight of sea salt;
  3.65% by weight of the total water weight of vegetable glycerin;
  0.83% by weight of the total water weight of ascorbic acid; and
  0.26% by weight of the total water weight of citric acid.

In another embodiment, the cold relief composition may be administered before coming into contact with potential germs such as crowded environments, malls, schools, and airplanes.

While in the foregoing specification this invention has been described in relation to certain preferred embodiments thereof, and many details have been set forth for the purpose of illustration, it will be apparent to those skilled in the art that the invention is susceptible to additional embodiments and that certain details described herein can be varied considerably without departing from the basic principles of the invention.

What is claimed is:

1. A method of intranasally treating a human suffering from sinus pain, sinus pressure or nasal decongestion consisting essentially of:
  administering intranasally an internasal spray container consisting essentially of therapeutically effective amounts of capsicum and a component selected from the group consisting of rosemary extract and potassium sorbate to said human;
  wherein first relief of sinus pain, sinus pressure, or nasal decongestion in said human occurs within about 30 minutes.

2. The method of claim 1, wherein first relief of sinus pain, sinus pressure, or nasal decongestion in said human occurs within about 5 minutes.

3. The method of claim 1, wherein first relief of sinus pain, sinus pressure, or nasal decongestion in said human occurs within about 1 minute.

\* \* \* \* \*